United States Patent [19]

Varma

[11] Patent Number: 4,481,144

[45] Date of Patent: Nov. 6, 1984

[54] 17-SUBSTITUTED THIA-17-ALKYL(OR ALKENYL OR ALKYNYL)ANDROSTENES

[75] Inventor: Ravi K. Varma, Belle Mead, N.J.

[73] Assignee: E. R. Squibb & Sons, Inc., Princeton, N.J.

[21] Appl. No.: 576,668

[22] Filed: Feb. 3, 1984

[51] Int. Cl.$^3$ ................................................ C07J 5/00
[52] U.S. Cl. ............................ 260/397.45; 260/397.3
[58] Field of Search ..................................... 260/397.45

[56] References Cited

U.S. PATENT DOCUMENTS

| | | | |
|---|---|---|---|
| 4,091,036 | 5/1978 | Varma | 260/397.45 |
| 4,094,840 | 6/1978 | Varma | 260/397.45 |
| 4,146,538 | 3/1979 | Varma et al. | 260/397.45 |
| 4,183,924 | 1/1980 | Green et al. | 260/397.1 |
| 4,252,733 | 2/1981 | Varma | 260/397.45 |
| 4,265,815 | 5/1981 | Varma | 260/397.45 |
| 4,361,559 | 11/1982 | Varma | 260/397.45 |

*Primary Examiner*—Elbert L. Roberts
*Attorney, Agent, or Firm*—Lawrence S. Levinson; Donald J. Barrack

[57] ABSTRACT

Antiinflammatory activity is exhibited by steroids having the formula

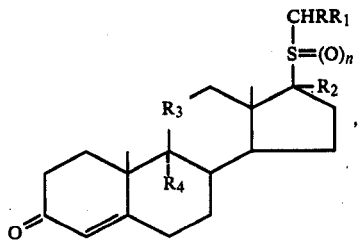

and the 1,2-dehydro derivatives thereof, wherein
R is hydrogen, alkyl, or aryl;
$R_1$ is hydrogen, alkyl,

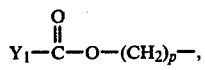

alkylthio, alkoxy, fluoro, hydroxyalkyl, cyanoalkyl, alkoxycarbonyl-$(CH_2)_p$-, mono-, di- or trifluoromethyl, or

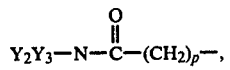

wherein p is 0, 1, 2, 3 or 4, $Y_1$ is alkyl or aryl, and $Y_2$ and $Y_3$ are the same or different and each is hydrogen or alkyl;
$R_2$ is alkyl, alkenyl or alkynyl;
$R_3$ is carbonyl or $\beta$-hydroxymethylene;
$R_4$ is hydrogen or halogen;
$R_5$ is hydrogen, methyl or fluorine; and
n is 0, 1 or 2.

24 Claims, No Drawings

17-SUBSTITUTED THIA-17-ALKYL(OR ALKENYL OR ALKYNYL)ANDROSTENES

BACKGROUND OF THE INVENTION

U.S. Pat. No. 4,361,559, issued Nov. 30, 1982, discloses (as antiinflammatory agents) 3-ketoandrostenes having in the 17-position the substituents $A_1$—S— and $A_2$—S— wherein $A_1$ and $A_2$ are the same or different and each is alkyl, cycloalkyl or aryl.

U.S. Pat. No. 4,094,840, issued June 13, 1978, discloses (as antiinflammatory agents) androstenes having the partial structural formula

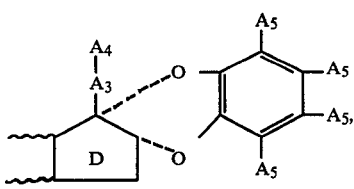

wherein $A_3$ is —S—,

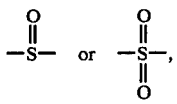

$A_4$ is alkyl, aryl, acyloxyalkyl, and the $A_5$ groups are halogen.

U.S. Pat. No. 4,091,036, issued May 23, 1978, discloses (as antiinflammatory agents) androstenes having the partial structural formula

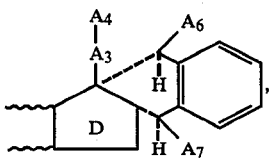

wherein $A_3$ and $A_4$ are as defined above, and $A_6$ and $A_7$ are the same or different and are hydrogen, alkyl, alkoxy, carboalkoxy, formyl,

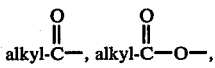

hydroxy, halogen, phenyl or cyano, with the proviso that when $A_6$ and $A_7$ are different, one of $A_6$ and $A_7$ is hydrogen.

U.S. Pat. No. 4,146,538, issued Mar. 27, 1979, discloses (as antiinflammatory agents) androstenes having the partial structural formula

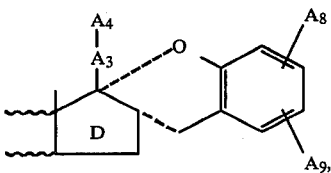

wherein $A_3$ and $A_4$ are as defined above, and $A_8$ and $A_9$ are the same or different and are hydrogen, halogen, alkyl, or alkoxy, or $A_8$ and $A_9$ together with the benzene ring to which they are attached form a naphthalene group.

U.S. Pat. No. 4,265,815, issued May 5, 1981 discloses (as chemical intermediates) androstenes having the partial structural formula

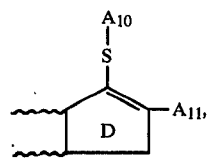

wherein $A_{10}$ is alkyl, aryl, arylalkyl or acyloxyalkyl and $A_{11}$ is chloro, bromo, alkoxy, aryloxy, alkylthio or arylthio.

U.S. Pat. No. 4,252,733, issued Feb. 24, 1981, discloses (as antiinflammatory agents) androstenes having the partial structural formula

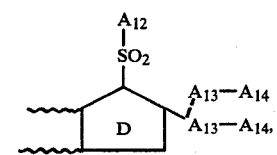

wherein $A_{12}$ is alkyl or aryl, $A_{13}$ is oxygen or sulfur and $A_{14}$ is alkyl or arylalkyl, or together the $A_{14}$ groups are —$(CH_2)$—$_{2\ or\ 3}$.

SUMMARY OF THE INVENTION

Steroids having the formula

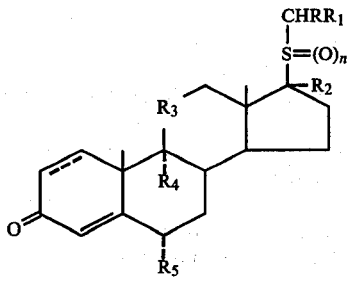

have antiinflammatory activity. In formula I, and throughout the specification, the symbols are as defined below.

R is hydrogen, alkyl, or aryl;
$R_1$ is hydrogen, alkyl,

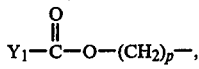

alkylthio, alkoxy, fluoro, hydroxyalkyl, cyanoalkyl, alkoxycarbonyl—$(CH_2)_p$—, mono-, di- or trifluoroalkyl, or

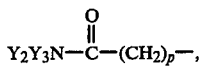

wherein p is 0, 1, 2, 3 or 4, $Y_1$ is alkyl or aryl, and $Y_2$ and $Y_3$ are the same or different and each is hydrogen or alkyl;
$R_2$ is alkyl, alkenyl or alkynyl;

$R_3$ is carbonyl or $\beta$-hydroxymethylene;
$R_4$ is hydrogen or halogen;
$R_5$ is hydrogen, methyl or fluorine; and
n is 0, 1 or 2.

The dotted line in the 1,2-position of the structural formulas shown in this specification indicate the optional presence of ethylenic unsaturation.

The term "aryl", as used throughout the specification either individually or as part of a larger group, refers to phenyl or phenyl substituted with one, two or three alkyl, alkoxy or halogen groups.

The term "halogen", as used throughout the specification either individually or as part of a larger group, refers to fluorine, chlorine, bromine and iodine.

The terms "alkyl" and "alkoxy", as used throughout the specification either individually or as part of a larger group, refer to groups having 1 to 12 carbon atoms.

The terms "alkanoyl", "alkenyl", and "alkynyl", as used throughout the specification either individually or as part of a larger group, refer to groups having 2 to 13 carbon atoms.

DETAILED DESCRIPTION OF THE INVENTION j

The steroids of formula I, and the 1,2-dehydro and 6,7-dehydro derivatives thereof, are topical antiinflammatory agents that can be used to treat skin conditions such as dermatitis, psoriasis, sunburn, eczema, neurodermatitis, or anogenital pruritus, and inhalation therapy for topical treatment of allergy and asthma.

For the treatment of skin conditions, the topical antiinflammatory steroids of this invention may be administered in a conventional pharmaceutical carrier in the form of a cream, ointment, lotion or the like. The steroids will preferably be used in the range of 0.01 to 5.0% by weight of the vehicle, preferably 0.05 to 2.0% by weight of the vehicle.

For the topical treatment of allergy and asthma the topical antiinflammatory steroids of this invention may be administered in the conventional manner, e.g., as solid medicament which has been atomized. U.S. Pat. Nos. 3,948,264 and 4,147,166 are exemplary of the literature which describes devices that can be used to administer solid medicaments for inhalation therapy.

The steroids of formula I can be prepared from the corresponding thione having the formula

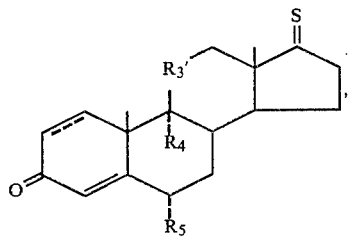

wherein $R_3'$ is carbonyl or $\beta$-acetyloxymethylene. These steroids are disclosed in U.S. patent application Ser. No. 462,164, filed Apr. 7, 1983.

Reaction of an androstene of formula II with a reagent having the formula $$R_2\text{—CuX}_1,\qquad \text{III}$$

wherein $X_1$ is $R_2Li$, $R_2Mg$-halogen, LiCN, or a trivalent phosphorous compound such as triphenylphosphine or hexamethylphosphorous triamide yields a steroid having the formula

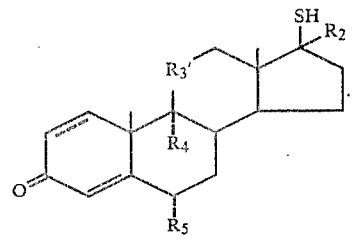

The steroids of formula IV are novel intermediates, and as such, constitute an integral part of this invention. Preferably, $X_1$ is LiCN, and the reaction is carried out in an organic solvent such as ethyl ether or tetrahydrofuran, or mixtures thereof.

The steroid of formula IV can be alkylated in situ (i.e., without isolation and purification) using a reagent having the formula $$RR_1CH\text{—}X_2, \qquad V$$

wherein $X_2$ is a traditional leaving group such as halogen, methanesulfonyl, or p-toluenesulfonyl, to yield the corresponding compound having the formula

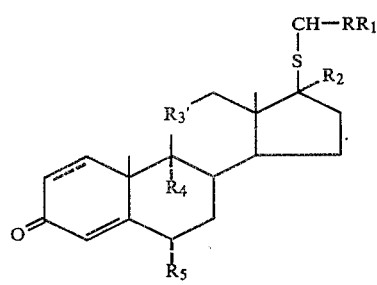

The compounds of formula VI are isomeric at the 17-position; the isomers can be separated by chromatography. Alternatively, the 17-thiol steroid of formula IV can be isolated, the isomers separated by chromatography, and each isomer alkylated with a compound of formula V in the presence of an organic or inorganic base in an ether or dimethylformamide sovlent.

The 11-acetate protecting group of a steroid of formula VI can be hydrolyzed with aqueous inorganic base (e.g., sodium hydroxide) to yield the products of formula I wherein n is 0, i.e., a steroid having the formula

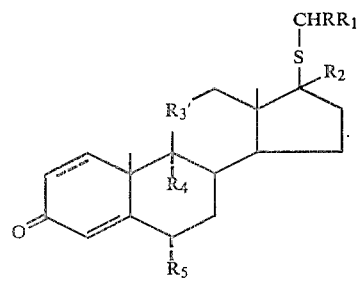

The sulfides of formula VII can be oxidized to the corresponding sulfinyl steroids (products of formula I, n is 1) or sulfonyl steroids (products of formula I, n is 2)

with peracids (e.g., m-chloroperoxybenzoic acid or periodic acid). The use of one equivalent of oxidizing agent will yield predominantly a sulfoxide and the use of two or more equivalents of oxidizing agent will yield predominantly a sulfone. The oxidation reaction can be run in an organic solvent, e.g., a halogenated hydrocarbon such as chloroform. Alternatively, the sulfonyl steroids of formula I can be prepared by oxidizing the corresponding sulfinyl steroid.

Alternative routes for the preparation of the steroids of formula I will be apparent to the practitioner of this invention. For example, those products of formula I wherein $R_1$ is

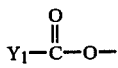

and n is 0 can be prepared by acylating the corresponding product of formula I wherein $R_1$ is hydrogen and n is 1. The acyloxy group can be displaced with an alkylthio or alkoxy group by reaction with a thiol or alcohol in the presence of a Lewis acid (e.g., boron trifluoride etherate) or an anhydrous protic acid (e.g., p-toluenesulfonic acid, hydrochloric acid, or trifluoroacetic acid).

The following examples are specific embodiments of this invention.

EXAMPLE 1

($11\beta,17\alpha$) and ($11\beta,17\beta$)-9-Fluoro-11-hydroxy-17-methyl-17-(methylthio)androsta-1,4-diene-3-one (A)

($11\beta$)-9-Fluoro-11-(acetyloxy)androsta-1,4-diene-3-one-17-thione

Dry benzene (250 ml) was refluxed for 30 minutes in a previously flamed flask using a soxhlet extractor filled with 5A molecular sieves. The solvent was cooled and to this was added a solution of ($11\beta,17\beta$)-9-fluoro-11-(acetyloxy)-17-(methylthio)-17-mercaptoandrosta-1,4-diene-3-one (9.2 g) in 50 ml of dry benzene and 15 drops of 1,8-diazabicyclo[5.4.0]undec-7-ene (300 mg). The reaction mixture was refluxed for 30 minutes, treated with acetic acid (1 ml), cooled and evaporated to dryness. The resulting syrup was dissolved in 1.0 liters of chloroform and was washed successively with 5% hydrochloric acid (210 ml) and water (225 ml). The organic phase was dried over anhydrous magnesium sulfate, filtered and evaporated to dryness. Yield: 9.34 g, reddish syrup.

The crude product mixture was dissolved in chloroform:hexane (6:4; 50 ml) and flash chromatographed on a silica gel column, eluting the column with 27.0 liters of chloroform:hexane (6:4). Fractions containing the thione and a trace of the starting material were combined and evaporated containing the pure thione were likewise combined and evaporated to dryness. Yield: 2.81 g. Both products were combined and crystallized from methanol to afford the title compound as salmon-colored crystals, melting point 155°–156° C.

(B) ($11\beta,17\alpha$) and ($11\beta,17\beta$)-11-(acetyloxy)-9-fluoro-17-methyl-17-(methylthio)androsta-1,4-diene-3-one Dry cuprous iodide (7.59 g; 0.04 mole) was suspended in 140 ml of dry tetrahydrofuran, cooled to 0° C. and treated portionwise under nitrogen with 0.96M methyl lithium (80 ml; 0.077 mole). The mixture was stirred at 0° C. for 15 minutes.

9-Fluoro-11-(acetyloxy)androsta-1,4-diene-3-one-17-thione (2.94 g; 0.0078 mole) was dissolved in dry tetrahydrofuran (55 ml) and added portionwise to the cooled complex. The reaction mixture was stirred at 0° C. under nitrogen for 3 hours after which 9.8 ml of methyl iodide was added. The reaction mixture was allowed to warm to room temperature and stirring continued overnight. The solution was quenched by pouring it into 10% ammonium chloride (500 ml) under stirring. The bluish solution with a yellowish top layer was extracted twice with 250 ml portions of chloroform. The organic phase was dried over anhydrous magnesium sulfate, filtered and the clear filtrate was stripped to dryness. Yield: 3.4 g, syrup.

Flash chromatography of the crude product twice on a silica gel column using chloroform:hexane (6:4) as eluent gave the $17\alpha$ isomer of the title compound. Yield: 530 mg. Additional products obtained from this reaction were ($11\beta,17\beta$)-11-(acetyloxy)-9-fluoro-17-methyl-17-(methylthio)-androsta-1,4-dien-3-one (293 mg) and ($11\beta,17\beta$)-11-(acetyloxy)-9-fluoro-17-(methylthio)androsta-1,4-diene-3-one (140 mg).

(C)

($11\beta,17\alpha$)-9-Fluoro-11-hydroxy-17-methyl-17-(methylthio)androsta-1,4-diene-3-one ($11\beta,17\alpha$)-11-(acetyloxy)-9-fluoro-17-methyl-17-(methylthio)androsta-1,4-diene-3-one (530 mg) was dissolved in 15.7 ml of tetrahydrofuran, 23 ml of methanol and 0.78 ml of water. Nitrogen was bubbled through the solution for 10 minutes after which the solution was treated with 0.78 ml of 12% sodium hydroxide. The mixture was stirred at room temperature under nitrogen for 1.5 hours, acidified with 0.4 ml of glacial acetic acid and stirred for 10 minutes. The solution was then evaporated to a slurry, diluted with water (50 ml) and stirred overnight. The white precipitate that formed was extracted twice with 50 ml portions of chloroform and the organic phase was dried over anhydrous magnesium sulfate, filtered and the clear filtrate evaporated to dryness. Yield: 510 mg.

The above product was combined with those from other runs and the entire mixture (1.0 g) was flash chromatographed on a silica gel column and stripped to dryness. Yield: 399 mg. This was combined with previous batches; total amount was 630 mg. Further purification on another column gave 575 mg of pure title compound, melting point 213°–215° C., $[\alpha]_D^{25}+64.7°$ (c, 0.45; chloroform).

Anal. Calc'd. for $C_{21}H_{29}FO_2S$: C, 69.20; H, 8.02; S, 8.80; F, 5.21. Found: C, 69.01; H, 8.12; S, 8.51; F, 4.95.

(D)

($11\beta,17\beta$)-9-Fluoro-$11\beta$-hydroxy-17-methyl-17-(methylthio)androst-1,4-diene-3-one A mixture of ($11\beta,17\alpha$) and ($11\beta,17\beta$)-11-(acetyloxy)-9-fluoro-17-methyl-17-(methylthio)-androsta-1,4-diene-3-one (850 mg) was reacted as described in part C above to yield 771 mg of a mixture of the title compound and its $17\alpha$-isomer. The mixture was flash chromatographed on a silica gel column using chloroform:hexane (6:4) as eluent to give the title compound (300 mg), melting point 227°–229° C., $[\alpha]_D^{25}+23.7°$ (c, 0.51; chloroform).

Anal. Calc'd. for $C_{21}H_{29}FO_2S$: C, 69.20; H, 8.02; F, 5.21; S, 8.80. Found: C, 68.84; H, 7.96; F, 4.98; S, 8.61.

EXAMPLE 2

$(11\beta,17\alpha)$-17-Butyl-9-fluoro-11-hydroxy-17-(methylthio)androsta-1,4-diene-3-one

(A) $(11\beta,17\alpha)$ and $(11\beta,17\beta)$-11$\beta$-(Acetyloxy)-9-fluoro-17-butyl-17-(methylthio)androsta-1,4-diene-3-one A suspension of cuprous cyanide (2.83 g, 0.0316 mole) in dry tetrahydrofuran (110 ml) was stirred in a bath at $-78°$ C. under an atmosphere of nitrogen and 1.7M n-butyllithium in hexane (16.9 ml, 0.0287 mole) was added dropwise. The mixture was then stirred at $-78°$ C. for 1.0 hour. A solution of $(11\beta)$-11-(acetyloxy)-9-fluoroandrosta-1,4-diene-3-one-17-thione (2.7 g, 0.0072 mole) in dry tetrahydrofuran (20 ml) was then added dropwise and was stirred at $-78°$ C. for 30 minutes; $-55°$ to $-60°$ C. for 45 minutes and $-20°$ to $-25°$ C. for 1.5 hours. Methyl iodide (9.0 ml) was added, the mixture was gradually warmed to room temperature and stirred for 18 hours. It was then poured into a 10% ammonium chloride solution (150 ml) and stirred for 1.0 hour. The resulting suspension was extracted with chloroform (2×200 ml). The chloroform extracts were combined, washed with water (100 ml), dried (anhydrous magnesium sulfate), filtered and evaporated to dryness to yield a gummy solid (2.9 g).

The crude product mixture was flash chromatographed three times on silica gel columns, eluting the first two columns with ethyl acetate:hexane (1:2) and the third column with chloroform:ethyl acetate (9:1). Yield: 1.6 g; ~50:50 mixture of the stereoisomers.

(B) $(11\beta,17\alpha)$ and $(11\beta,17\beta)$-17-Butyl-9-fluoro-11-hydroxy-17-(methylthio)androsta-1,4-diene-3-one $(11\beta,17\alpha)$ and $(11\beta,17\beta)$-11-(Acetyloxy)-9-fluoro-17-butyl-17-(methylthio)androsta-1,4-diene-3-one (500 mg; 1.1 mmole) was dissolved in a mixture of 13.6 ml of tetrahydrofuran, 6.7 ml of methanol and 0.67 ml of water. Nitrogen was bubbled into this solution for 20 minutes, after which it was treated with 12% sodium hydroxide (6.6 ml). The mixture was stirred under nitrogen for 1.5 hours, treated with 0.35 ml of glacial acetic acid. The mixture was stirred for 10 minutes, evaporated in vacuo to a slurry, diluted with water (50 ml) and stirred overnight. The precipitate that formed was filtered off, washed well with water and dissolved in methylene chloride. The organic solution was dried over anhydrous magnesium sulfate, filtered, and the clear filtrate evaporated to dryness. Yield: 456 mg.

The crude product mixture was mixed with material from a previous batch and the entire amount (678 mg) was dissolved in chloroform:hexane (3:2; 200 ml) and flash chromatographed on a silica gel column, eluting the column with chloroform:ethyl acetate (95:5). The fractions containing the desired product were combined and evaporated to dryness to yield 516.5 mg of the title compound as a mixture of two 17-stereoisomers.

The mixture (466 mg) was recrystallized from a mixture of methanol and methylene chloride. Yield: 176 mg, melting point 208°–210° C., $[\alpha]_D^{25}+41.3°$ (c, 0.45; chloroform).

Anal. Calc'd. for $C_{24}H_{35}FO_2S$: C, 70.90; H, 8.68; F, 4.67; S, 7.88. Found: C, 70.60; H, 8.54; F, 4.70; S, 7.70.

(C) $(11\beta,17\alpha)$-17-Butyl-9-fluoro-11-hydroxy-17-(methylthio)androsta-1,4-diene-3-one $(11\beta,17\alpha)$ and $(11\beta,17\beta)$-11-(Acetyloxy)-9-fluoro-17-butyl-17-(methylthio)-androst-1,4-diene-3-one (~1:1 mixture of C-17 stereoisomers; 900 mg) was dissolved in 100 ml of ethyl acetate:hexane:dichloromethane, (1:4:0.5) impregnated onto 10 g of silica gel and flash chromatographed on a silica gel column, eluting the column with ethyl acetate (1:4). The fractions containing the homogeneous 17α isomer were combined and evaporated to dryness. Yield: 200 mg of solid.

The above solid (179.3 mg) was dissolved in a mixture of 4.9 ml of tetrahydrofuran, 2.45 ml of methanol and 0.24 ml of water. Nitrogen was bubbled through the solution for 20 minutes after which it was treated with 2.4 ml of 12% sodium hydroxide. The reaction mixture was stirred at room temperature under nitrogen for 1.5 hours, treated with 0.13 ml of glacial acetic acid and stirred for ~10 minutes. The mixture was evaporated to a slurry, diluted with water (18 ml) and stirred overnight at room temperature. The precipitate that formed was filtered off, washed with a small amount of water and dissolved in methylene chloride (25 ml). The organic solution was dried over anhydrous magnesium sulfate, filtered and the clear filtrate evaporated to dryness. Yield: 167 mg of solid.

The solid was dissolved in 2.5 ml of dichloromethane:methanol (4:1), diluted with hexane (50 ml) and the solution concentrated to one-half its volume. The precipitate that formed was filtered off and dried overnight in vacuo at 40° C. Yield: 133 mg, melting point 185°–187° C., $[\alpha]_D^{25}+61.5°$ (c, 0.39, chloroform).

Anal. Calc'd. for $C_{24}H_{35}FO_2S$: C, 70.90; H, 8.68; F, 4.67; S, 7.88. Found: C, 70.90; H, 8.66; F, 4.70; S, 7.68.

EXAMPLE 3

$(11\beta,17\alpha)$-9-Fluoro-11-hydroxy-17-methyl-17-(methylsulfinyl)androsta-1,4-diene-3-one (sulfoxide isomers A&B)

$(11\beta,17\alpha)$-9-Fluoro-11-hydroxy-17-methyl-17α-(methylthio)androsta-1,4-diene-3-one (500 mg, 1.37 mmole) was dissolved in dichloromethane (40 ml), treated with a solution of 365.5 mg of 68% m-chloroperbenzoic acid (1.05 equiv.) in 10 ml of dichloromethane and stirred at room temperature for 20 minutes. The reaction mixture was quenched with 5% sodium carbonate solution (20 ml) and stirred for 15 minutes. The organic phase was separated and the aqueous phase extracted with dichloromethane (50 ml). All organic solutions were combined, dried over anhydrous magnesium sulfate and filtered. The clear filtrate was then evaporated to dryness. Yield: 600 mg of solid. This was dissolved in dichloromethane (12 ml) and chromatographed on three 2-mm preparative silica gel plates, developing the plates with chloroform:methanol (95:5) twice. Band II gave 209 mg of isomer A, which was crystallized from dichloromethane:hexane and the crystals obtained dried overnight in vacuo at 50%.

Yield: 186.6 mg, melting point 239°–240° C., $[\alpha]_D^{25}+25.7°$ (c, 0.23; chloroform)

Anal. Calc'd. for $C_{21}H_{29}FO_3S$: C, 65.51; H, 7.72; F, 4.93; S, 8.33 Found: C, 65.73; H, 7.55; F, 4.68; S, 8.22.

A second band from the preparative silica gel plates gave 180 mg of (isomer B). Recrystallization from dichloromethane:hexane followed by drying in vacuo at 50° C. gave 144 mg of isomer B, melting point 217°–218° C., $[\alpha]_D^{25} +51°$ (c, 0.21; chloroform).

Anal. Calc'd. for $C_{21}H_{29}FO_3S$: $0.75H_2O$: C, 64.01; H, 7.80; F, 4.82; S, 8.14 Found: C, 64.17; H, 7.68; F, 4.76; S, 8.01.

EXAMPLE 4

(11β,17β)-17-[[(Acetyloxy)methyl]thio]-9-fluoro-11-hydroxy-17-methylandrosta-1,4-diene-3-one (11β,17α)-9-Fluoro-11-hydroxy-17-methyl-17-(methylsulfinyl)androsta-1,4-diene-3-one (sulfoxide isomer mixture; see example 3) (456 mg; 1.46 mmole) was dissolved in dry benzene (45 ml) and treated with 0.135 ml of glacial acetic acid and 10 mg of p-toluenesulfonic acid hydrate. The reaction mixture was heated at 90° C. (oil bath) under nitrogen for 24 hours and then cooled and evaporated to dryness. Yield: 518 mg of solid.

The crude product mixture was subjected to preparative silica gel plates developing the plates with chloroform:ethyl acetate (1:1) (400 ml) and chloroform:ethyl acetate (1:9) (400 ml) to yield 148 mg of material. This was recrystallized first from dichloromethane:hexane (1:3) and then from acetone:hexane (1:3). The crystals obtained were dried overnight in vacuo at 90° C. Yield: 114 mg, melting point 210°–211° C., $[\alpha]_D^{25}+75.4°$ (c, 0.26; chloroform).

Anal. Calc'd. for $C_{23}H_{31}FO_4S$: C, 65.38; H, 7.39; F, 4.50; S, 7.59 Found: C, 65.20; H, 7.49, F, 4.60; S, 7.35.

EXAMPLE 5

(11β,17α)-17-Butyl-17-(ethylthio)-9-fluoro-11-hydroxyandrosta-1,4-diene-3-one

Dry cuprous cyanide (1.05 g, 11.72 mmole) was suspended in 40 ml of dry tetrahydrofuran and cooled to −78° C. (Dry ice-acetone bath) under nitrogen. A solution of 6.25 ml (10.62 mmole) of n-butyllithium (1.7M in hexane) was added under stirring. After stirring for one hour at −78° C., the suspension gradually became a brown homogeneous solution. A solution of 1.0 g (2.66 mmole) of (11β)-11-(acetyloxy)-9-fluoroandrost-1,4-diene-3-one, 17-thione in 7.0 ml of dry tetrahydrofuran was added dropwise to the above solution at −78° C. The mixture was stirred at −78° C. for 30 minutes and at −40° C. (Dry ice-acetonitrile bath) for 1.5 hours. Iodoethane (2.07 g, 13.28 mmole) was then added, and the mixture was gradually warmed to room temperature and stirred overnight. The resulting mixture was quenched with 30 ml of 25% ammonium chloride solution. After stirring for one hour the solid was removed by filtration, and the filtrate was diluted with water and extracted with chloroform (3×70 ml). The chloroform extracts were combined, washed with water, dried over anhydrous sodium sulfate and evaporated in vacuo to give 125 mg of a mixture of two stereoisomers of (11β)-11-(acetyloxy)-17-butyl-17-(ethylthio)-9-fluoroandrosta-1,4-diene-3-one.

The solid was suspended in 100 ml of chloroform and treated with 60 ml of 25% hydrochloric acid. After stirring for about one hour, the suspension gradually became a homogeneous two-layer solution. The chloroform layer was separated, washed with saturated sodium bicarbonate solution and water, dried over anhydrous sodium sulfate and evaporated in vacuo to give 300 mg of (11β,17α) and (11β,17β)-11-(acetyloxy)-17-butyl-9-fluoro-17-mercaptoandrosta-1,4-diene-3-one. This was dissolved in a small amount of chloroform and chromatographed on 4 precoated silica gel TLC plates (E. Merck, 20 cm×20 cm×0.5 mm, 4:6 ethyl acetate-hexane (4:6) for development) to give, in order of increasing polarity, the 17β isomer (142 mg) and the 17α isomer (138 mg).

To a suspension of 17 mg (0.35 mmole) of sodium hydride (50% in mineral oil) in 1.0 ml of dry dimethylformamide was added isomer B (75 mg, 0.17 mmole) at room temperature under nitrogen. After stirring for 2.0 hours, iodoethane (0.08 ml, 1.0 mmole) was added. The mixture was stirred overnight. A few drops of water was added and the stirring continued for about 1.0 hour. The resulting solution was poured into water and extracted with chloroform. The chloroform solution was dried over anhydrous sodium sulfate and evaporated in vacuo to give a gum. This was redissolved in a small amount of chloroform and chromatographed on a pre-coated silica gel TLC plate (E. Merck, 20 cm×20 cm×0.5 mm) using ethyl acetate-hexane (4:5) for development to give 36 mg of the title compound. Crystallization from ethyl acetate-hexane and drying gave 25 mg of a homogeneous analytical specimen, melting point 185°–187° C., $[\alpha]_D^{25}+70°$ (c, 0.4; chloroform).

Anal. Calc'd. for $C_{25}H_{37}FO_2S$: C, 71.38; H, 8.87; F, 4.52; S, 7.62 Found: C, 71.24; H, 9.03; F, 4.40; S, 7.38.

EXAMPLE 6

(11β,17α)-17-Butyl-9-fluoro-17-[(2-fluoroethyl)thio]-11-hydroxyandrosta-1,4-diene-3-one To a suspension of 9.6 mg (0.2 mmole) of sodium hydride (50% in mineral oil) in 0.4 ml of dry dimethylformamide was added 43.5 mg (0.1 mmole) of (11β,17α)-11-(acetyloxy)-17-butyl-9-fluoro-17-mercaptoandrosta-1,4-diene-3-one. After stirring at room temperature under nitrogen for 2.5 hours, 1-bromo-2-fluoroethane (0.05 ml, 0.67 mmole) was added and the stirring was continued overnight. A few drops of water was added and after stirring for one hour, the solution was poured into cold water extracted with chloroform. The chloroform solution was dried over anhydrous sodium sulfate and evaporated in vacuo to give an oil. Another run using 65.2 mg (0.15 mmole) of starting steroid gave more of the oily product. These oily products were combined and chromatographed on two pre-coated silica gel TLC plates, (E. Merck, 20 cm×20 cm×0.5 mm) using ethyl acetate-hexane (4:6) for development to give 67 mg of the title compound. Crystallization from ethyl acetate-hexane drying gave 50 mg of the tlc-homogeneous analytical specimen, melting point 181°–183° C. (dec.), $[\alpha]_D^{20}+64.5°$ (c, 0.4; chloroform).

Anal. Calc'd. for $C_{25}H_{36}F_2O_2S$: C, 68.46; H, 8.27; F, 8.66; S, 7.31 Found: C, 68.30; H, 8.28; F, 8.50; S, 7.12

EXAMPLE 7

(11β,17β)-17-Butyl-17-(ethylthio)-9-fluoro-11-hydroxyandrosta-1,4-diene-3-one

To a suspension of 9.6 mg (0.2 mmole) of sodium hydride (50% in mineral oil) in 0.4 ml of dry dimethylformamide was added 43.5 mg (0.1 mmole) of (11β,17β)-11-(acetyloxy)-17-butyl-9-fluoro-17-mercaptoandrosta-1,4-diene-3-one at room temperature under nitrogen. After stirring for 2.5 hours, iodoethane (0.08 ml, 1.0 mmole) was added and the stirring was continued overnight. A few drops of water were then added. After stirring for another hour, the solution was poured into water and extracted with chloroform. The chloroform solution was dried over anhydrous sodium sulfate and evaporated in vacuo to give a gum. This was chromatographed on a precoated silica gel TLC plate (E. Merck, 20 cm×20 cm×0.5 mm) using ethyl acetate-hexane (4:6) for development to give 20 mg of the title compound.

A solution of 75 mg (0.163 mmole) of (11$\beta$,17$\beta$)-11-(acetyloxy)-17-butyl-17-ethylthio-9-(fluoro)androsta-1,4-diene-3-one in methanol (4 ml) and water (4 drops) was stirred with 0.7 ml of 3M sodium hydroxide at room temperature under nitrogen for 1.5 hours. The resulting solution was quenched with a slight excess of acetic acid. The solvent was evaporated by a stream of nitrogen, and the resulting slurry was diluted with water and extracted with chloroform. The chloroform solution was washed with water, dried over anhydrous sodium sulfate and evaporated in vacuo to give an additional 52 mg of the title compound.

The two batches of the title compound were combined and crystallized from ethyl acetatehexane and dried to give 58 mg of analytical specimen, melting point 218°–220° C., $[\alpha]_D^{20}+32.8°$ (c, 0.47; chloroform).

Anal. Calc'd. for $C_{25}H_{37}FO_2S$: C, 71.38; H, 8.87; F, 4.52; S, 7.62 Found: C, 71.39; H, 8.91; F, 4.60; S, 7.56.

EXAMPLE 8

(11$\beta$,17$\beta$)-17-Butyl-9-fluoro-17-[(2-fluoroethyl)-thio]-11-hydroxyandrosta-1,4-diene-3-one Following the procedure of example 6, but substituting the 17-isomeric form of the starting steroid, yielded the title compound, melting point 213°–215° C., dec., $[\alpha]_D^{20}+29.3°$ (c, 0.54; chloroform).

Anal. Calc'd. for $C_{25}H_{36}F_2O_2S$: C, 68.46; H, 8.27; F, 8.66; S, 7.31 Found: C, 68.56; H, 8.37; F, 8.60; S, 7.33.

EXAMPLE 9

(11$\beta$,17$\beta$) and (11$\beta$,17$\alpha$)-9-Fluoro-11-hydroxy-17-(methylthio)-17-propylandrosta-1,4-diene-3-one (A) (11$\beta$,17$\beta$) and (11$\beta$,17$\beta$)-11-(Acetyloxy)-9-fluoro-17-(methylthio)-17-propylandrosta-1,4-diene-3-one Dry cuprous cyanide (1.05 g; 0.0117 mole) was suspended in dry, distilled tetrahydrofuran (55 ml), cooled to −40° to −50° C. and was treated with 10.33 ml of 1.08N propyllithium in ether (0.01064 mole) dropwise, with stirring in a nitrogen atmosphere. The resulting mixture was stirred at −40° to −50° C. for one hour resulting in a brown solution.

To the above solution was added (at −50° C.) a solution of 1.0 g (2.66 mmole) of (11$\beta$)-11-(acetyloxy)-9-fluoroandrost-1,4-diene-3-one-17-thione in 10 ml of dry tetrahydrofuran. The reaction mixture was stirred at −50° C. for 2.0 hours, at −40° C. for 1 hour, at −20° C. for 45 minutes, and at 0° C. for 1 hour. The reaction mixture was treated with methyl iodide (3.4 ml) at 0° C., allowed to warm to room temperature and stirred overnight under nitrogen. The solution was quenched with 25% ammonium chloride (30 ml), stirred for 30 minutes and the tetrahydrofuran evaporated. The suspension was diluted with water (30 ml), extracted twice with 100 ml portions of dichloromethane and the organic phase was dried over anhydrous magnesium sulfate. The mixture was filtered and evaporated to dryness. Yield: 1.09 g.

The above solid was suspended in methanol (10 ml) and stirred with 10% hydrochloric acid (3 ml) for 3 hours. The suspension was diluted with dichloromethane (100 ml), washed with water (50 ml) and the aqueous phase back-extracted with another 100 ml of dichloromethane. The organic extracts were combined, dried over anhydrous magnesium sulfate and filtered. The filtrate was evaporated to dryness and flash chromatographed twice on a silica gel column, eluting the column with ethyl acetate:hexane (1:3) to yield 150 mg of the (11$\beta$,17$\beta$) isomer and 706.5 mg of a mixture of the (11$\beta$,17$\alpha$) and (11$\beta$,17$\beta$) isomers.

(B) (11$\beta$,17$\beta$)-9-Fluoro-11-hydroxy-17-(methylthio)-17-propylandrosta-1,4-diene-3-one 150 mg (0.35 mmole) of (11$\beta$,17$\beta$)-11-(acetyloxy)-9-fluoro-17-(methylthio)-17-propylandrosta-1,4-diene-3-one was dissolved in a mixture of tetrahydrofuran (4.4 ml), methanol (2.16 ml) and water (0.21 ml). Nitrogen was bubbled through the solution for 20 minutes after which it was treated with 12% sodium hydroxide (0.21 ml) and stirred at room temperature under nitrogen for 1.5 hours. The reaction mixture was acidified with glacial acetic acid (0.11 ml), stirred for 30 minutes and evaporated to dryness. The solid obtained was suspended in water (15 ml) and stirred for 24 hours. The suspension was extracted with chloroform (100 ml) and the organic phase was dried over anhydrous magnesium sulfate and filtered. The clear filtrate was stripped to dryness to yield 175 mg. This was recrystallized from a mixture of dichloromethane:hexane (1:6) and the white crystals and dried in vacuo at room temperature over the weekend and at 90° C. for 3 hours to yield 124.1 mg of the 17$\beta$-isomer, melting point 237°–239° C., $[\alpha]_D^{25}+68.5°$ (c, 0.27; chloroform).

Anal. Calc'd. for $C_{23}H_{33}FO_2S$: C, 70.37; H, 8.47; F, 4.84; S, 8.17 Found: C, 70.21; H, 8.66; F, 4.60; S, 7.84.

(C) (11$\beta$,17$\alpha$)-9-Fluoro-11-hydroxy-17-(methylthio)-17-propylandrosta-1,4-diene-3-one 706.5 mg (0.0016 mole) of the impure (11$\beta$,17$\alpha$)-11-(acetyloxy)-9-fluoro-17-(methylthio)-17-propylandrosta-1,4-diene-3-one was dissolved in a mixture of tetrahydrofuran (19.8 ml), methanol (9.85 ml) and water (0.97 ml). Nitrogen was bubbled through the solution for 20 minutes, after which it was treated with 0.97 ml of 12% sodium hydroxide and stirred at room temperature under nitrogen for 1.5 hours. The reaction mixture was acidified with glacial acid (0.5 ml), stirred for 30 minutes and then evaporated to dryness. The solid obtained was suspended in 59 ml of water, stirred at room temperature for 20 hours and the aqueous suspension was extracted with chloroform (150 ml) twice. The organic phase was dried over anhydrous magnesium sulfate, filtered and the clear filtrate evaporated to dryness. The crude product mixture was dissolved in 100 ml of chloroform:hexane (3:2), impregnated onto 5.0 g of silica gel and flash chromatographed on a silica gel column, eluting the column sccessively with chloroform:hexane (4:1, 2.5 liters) and chloroform:hexane (9:1, 2.0 li.). The desired fractions were combined and evaporated to dryness, yield: 183.5 mg of solid. This was crystallized from acetone:hexane (1:7; 115 ml) concentrating the cloudy solution to a volume of 25 ml. The white crystals that formed were filtered off and dried overnight in vacuo at 90° C. to yield 120.4 mg of the 17$\alpha$-isomer, melting point 234°–235° C., $[\alpha]_D^{25}+38.7°$ (c, 0.23, chloroform).

Anal. Calc'd. for $C_{23}H_{33}FO_2S$: C, 70.37; H, 8.47; F, 4.84; S, 8.17 Found: C, 70.15; H, 8.51; F, 4.80; S, 8.05.

EXAMPLE 10

$(11\beta,17\alpha)$ and $(11\beta,17\beta)$-17-Ethyl-9-fluoro-11-hydroxy-17-(methylthio)-androsta-1,4-diene-3-one Following the procedure of example 9, parts A & B, but substituting ethyllithium for propyllithium, yielded the title compound, melting point 252°–254° C., $[\alpha]_D^{25} + 39.5°$ (c, 0.22; chloform).

Anal. Calc'd. for $C_{22}H_{31}FO_2S$: C, 69.80; H, 8.25; F, 5.02; S, 8.47 Found: C, 69.77; H, 8.25; F, 4.90; S, 8.38.

What is claimed is:

1. A steroid having the formula

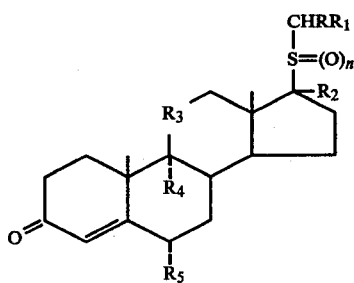

or a 1,2-dehydro derivative thereof, wherein
R is hydrogen, alkyl or aryl;
$R_1$ is hydrogen, alkyl,

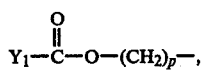

alkylthio, alkoxy, fluoro, hydroxyalkyl, cyanoalkyl, alkoxycarbonyl—$(CH_2)_p$—, mono-, di- or trifluoroalkyl or

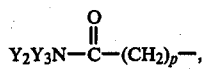

wherein p is 0, 1, 2, 3, or 4, $Y_1$ is alkyl or aryl, and $Y_2$ and $Y_3$ are the same or different and each is hydrogen or alkyl;
$R_2$ is alkyl, alkenyl or alkynyl;
$R_3$ is carbonyl or $\beta$-hydroxymethylene;
$R_4$ is hydrogen or halogen;
$R_5$ is hydrogen, methyl or fluorine; and
n is 0, 1 or 2.

2. A steroid in accordance with claim 1 having the formula

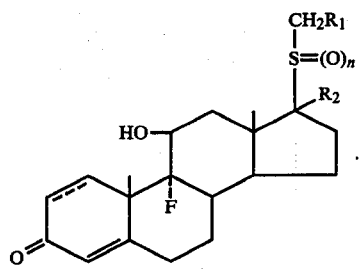

3. A steroid in accordance with claim 1 wherein R is hydrogen.

4. A steroid in accordance with claim 1 wherein R is alkyl.

5. A steroid in accordance with claim 1 wherein R is aryl.

6. A steroid in accordance with claim 1 wherein $R_1$ is hydrogen.

7. A steroid in accordance with claim 1 wherein n is 0.

8. A steroid in accordance with claim 1 wherein n is 1.

9. A steroid in accordance with claim 1 wherein n is 2.

10. A steroid in accordance with claim 1 wherein $R_2$ is alkyl.

11. A steroid in accordance with claim 2 wherein $R_2$ is alkyl.

12. The steroid in accordance with claim 1, $(11\beta,17\alpha)$-9-fluoro-11-hydroxy-17-methyl-17-(methylthio)androsta-1,4-diene-3-one.

13. The steroid in accordance with claim 1, $(11\beta,17\beta)$-9-fluoro-11-hydroxy-17-methyl-17-(methylthio)androsta-1,4-diene-3-one.

14. The steroid in accordance with claim 1 $(11\beta,17\alpha)$-17-butyl-9-fluoro-11-hydroxy-17-(methylthio)androsta-1,4-diene-3-one.

15. The steroid in accordance with claim 1, $(11\beta,17\alpha)$-9-fluoro-11-hydroxy-17-methyl-17-(methylsulfinyl)androsta-1,4-diene-3-one.

16. The steroid in accordance with claim 1, $(11\beta,17\beta)$-17-[[(acetyloxy)methyl]thio]-9-fluoro-11-hydroxy-17-methylandrosta-1,4-diene-3-one.

17. The steroid in accordance with claim 1 $(11\beta,17\alpha)$-17-butyl-17-(ethylthio)-9-fluoro-11-hydroxyandrosta-1,4-diene-3-one.

18. The steroid in accordance with claim 1, $(11\beta,17\alpha)$-17-butyl-9-fluoro-17-[(2-fluoroethyl)thio]-11-hydroxyandrosta-1,4-diene-3-one.

19. The steroid in accordance with claim 1, $(11\beta,17\beta)$-17-butyl-17-(ethylthio)-9-fluoro-11-hydroxyandrosta-1,4-diene-3-one.

20. The steroid in accordance with claim 1, $(11\beta,17\beta)$-17-butyl-9-fluoro-17-[(2-fluoroethyl)-thio]-11-hydroxyandrosta-1,4-diene-3-one.

21. The steroid in accordance with claim 1, $(11\beta,17\alpha)$-9-fluoro-11-hydroxy-17-(methylthio)-17-propylandrosta-1,4-diene-3-one.

22. The steroid in accordance with clarm 1, $(11\beta,17\beta)$-9-fluoro-11-hydroxy-17-(methylthio)-17-propylandrosta-1,4-diene-3-one.

23. The steroid in accordance with claim 1 $(11\beta,17\alpha)$ and $(11\beta,17\beta)$-17-ethyl-9-fluoro-11-hydroxy-17-(methylthio)androsta-1,4-diene-3-one.

24. A steroid having the formula

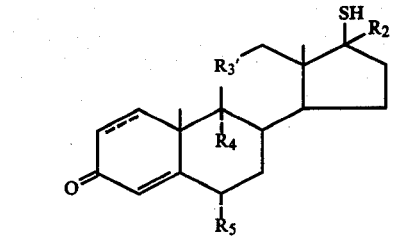

wherein
$R_2$ is alkyl, alkenyl or alkynyl;
$R_3'$ is carbonyl or $\beta$-acetyloxymethylene;
$R_4$ is hydrogen or halogen; and
$R_5$ is hydrogen, methyl or fluorine.

* * * * *

UNITED STATES PATENT AND TRADEMARK OFFICE
CERTIFICATE OF CORRECTION

PATENT NO. : 4,481,144
DATED : November 6, 1984
INVENTOR(S) : Ravi K. Varma

It is certified that error appears in the above—identified patent and that said Letters Patent is hereby corrected as shown below:

Column 3, line 24, delete "j" after the word "Invention".

Column 11, line 39, delete "17β" and replace with --17α--.

Signed and Sealed this

Sixteenth Day of April 1985

[SEAL]

Attest:

DONALD J. QUIGG

Attesting Officer     Acting Commissioner of Patents and Trademarks